United States Patent [19]  
Schlicht

[11] 4,196,091  
[45] Apr. 1, 1980

[54] LACTAM CARBOXYLIC ACIDS, THEIR METHOD OF PREPARATION AND USE

[75] Inventor: Raymond C. Schlicht, Fishkill, N.Y.

[73] Assignee: Texaco Inc., White Plains, N.Y.

[21] Appl. No.: 865,107

[22] Filed: Dec. 27, 1977

[51] Int. Cl.$^2$ .............................................. C10M 1/32
[52] U.S. Cl. .............................. 252/51.5 A; 252/390; 260/326.45
[58] Field of Search .................... 252/51.5 A, 51.5 R, 252/390; 260/326.45

[56] References Cited

U.S. PATENT DOCUMENTS

| | | | |
|---|---|---|---|
| 2,757,125 | 7/1956 | Mudrak | 260/326.45 X |
| 2,908,711 | 10/1959 | Halter et al. | 260/326.45 X |
| 3,062,631 | 11/1962 | Thompson | 252/51.5 A X |
| 3,178,347 | 4/1965 | Bocher | 260/326.45 X |
| 3,218,264 | 11/1965 | Katz | 260/326.45 X |
| 3,219,666 | 11/1965 | Norman et al. | 252/51.5 A X |
| 3,224,968 | 12/1965 | Hinkamp | 252/51.5 A X |
| 3,224,975 | 12/1965 | Hinkamp | 252/51.5 A |
| 4,081,456 | 3/1978 | Heiba et al. | 252/51.5 R X |

*Primary Examiner*—Andrew Metz  
*Attorney, Agent, or Firm*—Robert A. Kulason; Carl G. Ries; James J. O'Loughlin

[57] ABSTRACT

This invention relates to hydrocarbyl lactam-carboxylic acids prepared by a reaction of a hydrocarbyl succinic anhydride with an imine and their use as corrosion inhibitors in crankcase lubricant compositions.

11 Claims, No Drawings

LACTAM CARBOXYLIC ACIDS, THEIR METHOD OF PREPARATION AND USE

BACKGROUND OF THE INVENTION

This invention relates to alkenyl lactam carboxylic acids useful as rust inhibitors in crankcase oil formulations and as intermediates in the production of valuable dispersants for use in fuels, transmission fluids and the like. The invention relates to the preparation of these lactam acids by reaction of an imine with an alkenyl succinic acid.

The Perkin condensation of benzaldehyde and succinic anhydride to form phenylparaconic acid has been well established in the public literature.

The condensation of benzylidene methyl amine with succinic acid anhydride to form, illustratively, low molecular weight carboxy butyrolactams has also been suggested. It is known, in addition, to prepare gamma-hydrocarbyl-substituted gamma-butyrolactone acetic acids by acid hydrolysis of alkenylsuccinic anhydrides. It has also been proposed to react alkylene polyamines, monocarboxylic acids or their anhydrides and thereafter an alkenyl succinic acid or its anhydride and a metal salt to provide metal complexes useful as detergents in lubricating oils.

If, however, lactam carboxylic acids, and particularly alkenyl bis-lactam carboxylic acids and lactam carboxylic acids containing high molecular weight hydrocarbyl substituents, could be conveniently prepared using imines and alkenyl succinic anhydrides to this end, resulting in useful corrosion inhibitors for use in crankcase oils, and more particularly, valuable intermediates which, in reaction with various amines, form valuable derivatives which may be readily and conveniently produced and selectively adapted for use as dispersants as well as rust inhibitors for use in oils and the like, there would result a material and unexpected advance in the state of the art.

SUMMARY OF THE INVENTION

It is an object of this invention, therefore, to provide novel lactam carboxylic acids.

It is a further object of this invention to produce these acids by a novel, efficacious method.

It is a still further object of this invention to provide novel and useful corrosion inhibitors for incorporation in crankcase oils, and more particularly to provide intermediates in the preparation, by a novel, convenient and readily controlled and selective method, of products useful as dispersants in lubricating oils, and particularly those for use in diesel engines, outboard motors, and automatic transmission fluids.

These and other objects and advantages of this invention will become evident from the following description.

Accordingly, it has now been discovered that lactam carboxylic acids, and more particularly, and, predominantly, novel gamma-lactam acids useful as rust inhibitors in lubricant oils and as intermediates can be prepared by reaction of a hydrocarbyl succinic anhydride (or a hydrocarbyl succinyl halide) and preferably an alkenyl succinic anhydride with a variety of imines.

DETAILED DESCRIPTION OF THE INVENTION

The lactam carboxylic acids of the invention are gamma-lactam acids or 3-carboxy butyrolactams characterized by the general formula:

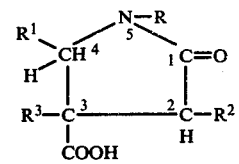

wherein:
R is a hydrocarbyl radical including an alkyl, aryl, alkaryl or aralkyl moiety, a mono- or di-substituted aminoalkyl radical wherein each of said alkyl groups contains from 1 to 12, and preferably 1 to 7, carbon atoms, or an N-(3-carboxy-butyrolactam) alkyl radical in which said alkyl moiety contains from 1 to 12, and preferably 2 to 6, carbon atoms, and said lactam radical contains, additionally, the substituents, $R^1$, $R^2$ and $R^3$, having the values provided herein;

$R^1$ is a hydrogen atom or a hydrocarbyl radical and, desirably, one of from 1 to 20 carbon atoms, including an alkyl, aryl, arakyl or alkaryl radical, and preferably a phenyl radical; and each of $R^2$ and $R^3$ is a hydrogen atom or a hydrocarbyl radical of from 1, and in a significantly preferred embodiment, from 10 to 500, and more desirably from 10 to 300, carbon atoms and an alkenyl moiety, provided that, in any event, only one of $R^2$ and $R^3$ is hydrogen and only one is, concomitantly, a hydrocarbyl radical.

The foregoing radicals, characterized as "hydrocarbyl" are intended to include one or more substituents from which active hydrogen atoms are absent, including alkoxyl, nitro, nitrile, carbalkoxyl, and tertiary amino moieties; and which are, with respect to those of the foregoing moieties occurring as substituents in each of the radicals represented by R, $R^1$, $R^2$ and $R^3$, less reactive, in any event, than an imino group.

Illustrative of the lactam acid products of the invention are, 2-polybutenyl-3-carboxy-4-phenyl-5-methyl butyrolactam; 3-dodecenyl-3-carboxy-4-phenyl-5-methyl butyrolactam; 2-dodecenyl-3-carboxy-4-phenyl-5-methyl butyrolactam; 3-polybutenyl-3-carboxy-4-phenyl-5-methyl butyrolactam; 2-polyisobutenyl-3-carboxy-4-phenyl-5-(N,N-dimethylaminoethyl) butyrolactam; 2-octadecenyl-3-carboxyl-4-phenyl-5-(N,N-dimethylamineothyl) butyrolactam; 1',2'-ethylene-bis-(3-polybutenyl-3-carboxy-4-phenyl-butyrolactam-5); 1',6'-hexylene-bis-(2-dodecenyl-3-carboxy-4-phenyl butyrolactam-5); 1',6'-hexylene-bis-N-(2-polybutenyl-3-carboxy-4-phenyl) butyrolactam-5); and isomeric mixtures thereof.

The process, according to the invention, of preparing the foregoing lactam acids comprises reacting a hydrocarbyl succinic acid anhydride (II) or hydrocarbyl substituted succinyl halide (III), respectively of the formulae:

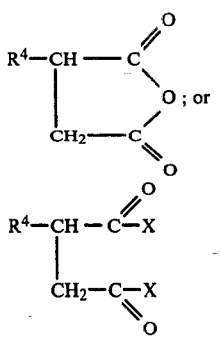

wherein X is a halogen atom, i.e. chlorine, bromine, iodine or fluorine, and preferably a chlorine atom; and $R^4$ is a hydrocarbyl radical of from 1, and in a significantly preferred embodiment, 10 to 500, and more desirably 10 to 300, carbon atoms, and is, most desirably, an alkenyl radical; with an imine of the formula:

$$R^1—CH=N—R^9 \qquad (IV)$$

wherein $R^1$ is a hydrogen atom or a hydrocarbyl radical, and preferably a benzylidene moiety, of from 1 to 20 carbon atoms; and $R^9$ is a hydrocarbyl radical of from 1 to 12 carbon atoms, a mono- or di-hydrocarbyl-substituted aminoalkyl radical in which each hydrocarbyl moiety and said alkyl moiety contains from 1 to 12 carbon atoms, or a hdyrocarbyliden-iminoalkyl radical, more desirably, one in which the alkyl substituent contains from 1 to 12 carbon atoms, and preferably a benzyliden-iminoalkyl radical wherein said alkyl group contains from 2 to 6 carbon atoms.

Illustrative and particularly preferred Schiff's bases or substituted imines for use in the foregoing reaction are: N,N'-ethylene-bis-benzylidenimine of the formula:

$$C_6H_5—CH=N—(CH_2)_2—N=CH—C_6H_5; \qquad (V)$$

N,N'-hexamethylene-bis-benzylidenimine of the formula:

$$C_6H_5CH=N—(CH_2)_6—N=CH—C_6H_5; \qquad (VI)$$

N-methylbenzylidenimine (benzylidene methyl amine) of the formula:

$$C_6H_5CH=N—CH_3; \text{ and} \qquad (VII)$$

3(N'N'-dimethylamino) propyl-N-benzylidenimine of the formula:

$$C_6H_5—CH=N—(CH_2)_3—N\begin{matrix}CH_3\\CH_3\end{matrix} \qquad (VIII)$$

Other illustrative imines coming within the purview of the present invention include N,N'-dodecylene-bis-p-cyanobenzylidenimine, N,N'-hexadecylene-m-dimethyl amino benzylidenimine-p'-chloro benzylidenimine,N,N'-eicosylene-bis-benzylidenimine, and 7-(N'-ethyl-N'phenyl amino) heptyl-N-benzylidenimine.

Significantly preferred for reaction with the foregoing imines, of the anhydrides and halides of formulae (II) and (III) referred to hereinabove, are the alkenyl succinic anhydrides wherein $R^4$ is an alkenyl radical and the aliphatic hydrocarbon moiety so defined is branched or straight-chain and contains from 10 to 300 carbon atoms.

The foregoing alkenyl substituents are also preferred in the substituted succinyl halides represented in formula (III) wherein $R^4$ constitutes the halides' alkenyl substituent. These halides are, in any event, significantly less preferred in the practice of the invention.

The lactam acids formed by the foregoing reaction are, as indicated, predominantly the gamma-lactam acids. Minor amounts of the corresponding beta-lactam acids are, however, also secured according to the practice of the invention. These latter compounds, corresponding to the gamma-lactam acids of formula I above may be represented as follows:

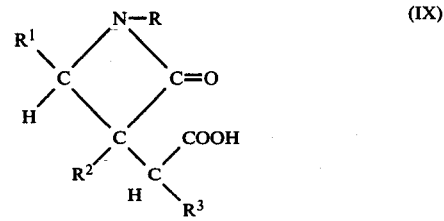

wherein each of R, $R^1$, $R^2$ and $R^3$ is as described hereinabove;

Isomeric mixtures of both the foregoing beta-, and predominant gamma-lactam acids result from the process as practiced by the present invention.

The foregoing anhydride (or acyl halide) and imine are reacted in a ratio of 1 mole of anhydride or acyl halide to each imino linkage present in the imine. Thus, for example, in a reaction of polybutene succinic anhydride with N,N'-ethylene-bis-benzylidenimine, which contains two imino groups, two moles of anhydride are reacted with each mole of imine. Where, again illustratively, polybutene succinic anhydride is reacted with 3-(N',N'-dimethylamino) propyl-N-benzylidenimine the molar ratio of anhydride to imine is 1:1.

The foregoing molar relationships are intended to describe the least amount of anhydride (or halide) that will react with all of the imine added to the reaction. Lesser molar amounts, and indeed molar amounts of anhydride (or halide) in excess of those recited can also be employed.

The reaction proceeds at ambient pressure in an inert atmosphere at a temperature of 50° C. to 200° C. for a period of 1 hour to 20 hours and preferably at a temperature of 80° C. to 120° C. for 1 hour to 5 hours, the reaction temperature being increased where the higher molecular weight alkenyl-substituted succinic anhydrides or succinic halides are used. Minor amounts of alkenyl succinimide are also obtained as a result of the reaction.

The product lactam acids whether of the gamma-lactam or beta-lactam configuration occur, as noted, in isomeric mixtures. The isomers involve the presence, predominantly, of the alkenyl (hydrocarbyl) moiety on the 2-carbon position, and less frequently, on the 3-carbon position of the butyrolactam, or expressed more generically so as to apply to both the gamma and beta lactam acids, the presence of the alkenyl (hydrocarbyl) substitutent on the carbon adjacent the carbonyl group or on the carbon to which the carboxy group is directly attached.

It is often feasible to use the gamma-lactam acid products without removal of the carboxy butyrolactams from the reaction product mixture either as a corrosion inhibitor in crankcase lubricant compositions, (as a lube oil detergent or dispersant) or as an intermediate in production of other compounds useful as dispersants in lubricant compositions. It is believed that imide byproducts, such as hydrocarbyl-, and usually, in terms of the preferred alkenyl succinic anhydride employed, alkenyl-, succinimide lactam acids or bis-imides may be present in the reaction product mixture.

As indicated hereinabove, the lactam acids prepared in accordance with the invention are effective as rust inhibitors when utilized in lubricant oil compositions, and particularly so, in crankcase lubricant compositions. They are effective dispersants as well when the alkenyl substituent is within the range of 10 to 20 carbon atoms, for example, where a dodecenyl moiety is present as $R^1$ in the lactam acids of formula (I) hereinabove.

The lactam acids of the invention, when employed as rust inhibitors (or dispersants), form a substantial, or even major, portion by volume of any lubricant composition of which they form a part.

A desirable lubricant composition for the purpose herein described has been found to be a fully formulated crankcase oil containing about 0.2 percent to about 10.0 percent by weight of one of the foregoing lactam acids, including a predominant portion of gamma-lactam acid, and, although not necessarily; a minor amount of beta-lactam acid. Preferred proportions of the lactam acid corrosion inhibitors of the invention in these crankcase oils are within the range of 0.5 percent to 7.0 percent by weight, and preferably from about 1.0 percent to 5.0 percent by weight.

The lubricant compositions of the invention are also fortified normally with conventional additives such as anti-foaming agents, dispersants, antioxidants, pour point depressants, viscosity index improvers, and other conventional additives such as described hereinafter.

A suitable anti-foaming agent for incorporation in the fully formulated crankcase oils of the invention is a dimethyl silicone polymer having a kinematic viscosity at 25° C. of about 100 centistokes and above. A very satisfactory anti-foaming agent for this purpose is prepared by diluting 10 grams of a dimethyl silicone polymer (1000 centistokes at 25° C.) with kerosene to provide a solution of 100 cubic centimeters. From 0.005 to 0.25 percent by weight of this concentrate is generally employed to provide from 50 to 200 parts per million of the silicone polymer based on the lubricating oil composition.

A metal, and desirably, a zinc dithiophosphate component desirably incorporated in the lubricating oil of the invention is one represented by the formula:

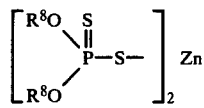

in which $R^8$ is a hydrocarbyl radical or a hydroxy-substituted hydrocarbyl radical having from 2 to 12 carbon atoms. The preferred zinc dithiophosphates are those in which R represents an alkyl radical having from 3 to 9 carbon atoms. Examples of suitable compounds include zinc isobutyl 2-ethylhexyl dithiphosphate, zinc di(2-ethylhexyl) dithiophosphate, zinc isoamyl 2-ethylhexyl dithiophosphate, zinc di(phenoxyethyl) dithiophosphate,zinc di(2,4-diethylphenoxyethyl) dithiophosphate and zinc isopropylmethyl isobutyl carbinyl dithiophosphate. In general, these compounds are employed in the oil composition in a concentration ranging from about 0.1 to 3.0 percent with the preferred concentration ranging from about 0.15 to 1.5 percent. These compounds can be prepared from the reaction of a suitable alcohol or mixture of alcohols with phosphorus pentasulfide. They are illustrated in U.S. Pat. Nos. 2,344,395 and 3,293,181.

Most desirable is the zinc alkyldithiophosphate prepared by reaction of 2.7 moles of a mixture of predominantly, that is up to 95 percent of $C_4$ to $C_9$ alcohols and 2–3 moles of isopropanol with 1.0 mole of $P_2S_5$. The zinc salt is then made by reaction of the dialkyldithiophosphoric acid with an excess of zinc oxide.

Ashless dispersants, the hydrocarbyl thiophosphonates represented by the formula:

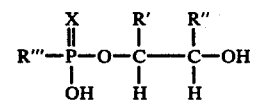

in which $R'''$ is a hydrocarbyl radical having at least 12 carbon atoms and $R'$ and $R''$ are selected from the group consisting of hydrogen and monovalent aliphatic hydrocarbyl radicals containing 1 to 6 carbon atoms, and X is predominantly, or normally, sulfur, may also be included in the lubricant compositions of the invention in amounts of 0.1 to 5 weight percent. However, preferred dispersants of this type, optionally employed herein, in the same concentrations are mono β-hydroethyl) alkene thiophosphonates, and, most desirably, those wherein the alkene substituent is polybutene (of an average molecular weight of about 1000 to 1500, i.e. 1290).

Used to provide a high level of alkalinity in the lubricant oil composition of the invention is a calcium carbonate overbased calcium sulfonate component containing from about 5 moles to 30 moles of dispersed calcium carbonate per mole of calcium sulfonate and having a Total Base Number from about 100 to 500. The preferred overbased calcium sulfonate will have from about 10 to 20 moles of dispersed calcium carbonate per mole of calcium sulfonate.

In general, an overbased calcium sulfonate is prepared by reacting a calcium sulfonate (derived from the reaction of a natural or synthetic sulfonic acid having a molecular weight ranging from about 350 to 600 with hydrated lime) with carbon dioxide at an elevated temperature, 135°–160° F., for an extended time period of several hours and under total reflux conditions. Thereafter the reaction mixture is filtered to recover an approximately 45 percent oil solution of calcium carbonate overbased calcium solution prescribed above. The preparation of this component is fully described in U.S. Pat. No. 3,537,996 and the disclosure of this reference is incorporated herein. This additive is incorporated in a finished lubricant oil in a concentration of 0.2 wt. percent to 6 wt. percent; and more desirably 0.2 wt. percent to 2 wt. percent.

Most desirably, there is employed, additionally, as a viscosity index improver, a copolymer of ethylene and propylene containing, in a preferred embodiment 30 to 50 percent propylene having a molecular weight of 20,000 to 50,000. This additive is incorporated in a diluent mineral oil such as 100 E Pale Stock HF or solvent Neutral Oils the proportions of copolymer therein varying, illustratively, from 15 to 20 weight percent. This additive is included in an amount by weight of 5% to 10%.

A further dispersant and viscosity index improving component also contemplated for use in the lubricant oils provided herein is a basic amine-containing addition-type copolymer formed of a plurality of polymerizable ethylenically unsaturated compounds, at least one of which is amino-free and contains from 8 to about 18 carbon atoms in an aliphatic hydrocarbon chain, preferably predominantly straight chain in nature, and one of which, as it exists in the polymer, contains a basic amino nitrogen in the side chain, in an amount by weight of said polymer of 0.05 to 3.5 percent.

It is essential that at least one of the monomeric components employed in making the polymer should introduce an oil-solubilizing or oleophilic structure to insure that the polymer is soluble to the extent of at least 0.1% by weight in naphthenic or paraffinic lubricating oils. In addition, the presence of basic amino groups, either primary, secondary or tertiary may be included optionally to impart additional sludge dispersing properties. Elaborating on the description provided hereinabove, introduction of the basic amino nitrogen structure can be accomplished by the use of at least one monomeric component containing the amino group or by use of a monomer containing a group which is reactive, when present in the polymer, toward ammonia, or primary or secondary non-aromatic amines. These monomers can also contain oleophilic structures that will assist in contributing to the requisite oil solubility. In addition, some of the polymers coming within the scope of this invention can, without sacrificing either oil solubility or dispersing properties, include certain proportions of monomers that do not themselves yield oil soluble polymers.

Desirably, these additional components include about 0.25 to 8.0 weight percent of an oil concentrate containing a polymer of mixed alkyl esters of methacrylic acid having a molecular weight of from about 25,000 to 1,250,000 and preferably where the polymer is to be used as a pour depressant in the range of 25,000 to 50,000. Where its predominant contribution is as a viscosity index improver a molecular weight in excess of 50,000 and within the broader range recited is employed. The foregoing alkyl methacrylate esters are desirably, and usually, mixtures of the foregoing esters wherein the alkyl substituents are straight chained and contain from about 4 to 22 carbon atoms.

Particularly useful pour depressants are the methacrylate esters of $C_4$ to $C_{22}$ primary linear saturated aliphatic alcohols, incorporated in a concentration of up to 33 weight percent in a diluent mineral oil such as 100 E Pale Stock HF.

Further illustrative of these preferred methacrylate-containing polymers are the copolymer of butyl, lauryl, stearyl and dimethaminoethyl methacrylate wherein the butyl, lauryl, stearyl and dimethylamino monomers are incorporated in a weight ratio respectively of 21:53:22:4. It should be understood, additionally, that lauryl methacrylate monomer charged to the polymerization reaction frequently contains about 25 percent to 28 percent by weight of myristyl methacrylate and the stearyl methacrylate monomer includes, by weight, about 32 percent to 44 percent of cetyl methacrylate and possibly up to 16 percent by weight of lower hydrocarbyl-containing methacrylates.

Conventional amine antioxidants are also desirably included in the lubricant compositions of the invention; exemplified by the phenyl naphthylamines, and particularly phenyl beta naphthylamine, phenylene diamine, phenothiazine, diphenylamine and preferably, in many instances, mixed alkylated aromatic amines such as a trialkyl substituted diphenyl amine. Particularly preferred concentrations of antioxidant in the formulation of lube oil concentrates are within the range of about ten (10) to about fifty (50) weight percent. Preferred concentrations of these amines in the finished motor oil compositions are within the range of about 0.1 to about 10 weight percent.

The hdyrocarbon mineral oils employed in this invention can be paraffin base, naphthene base, or mixed paraffin-naphthene base distillate or residual oils. The lubricating oil base generally has been subjected to solvent refining to improve its lubricity and viscosity temperature relationship as well as solvent dewaxing to remove waxy components and to improve the pour of the oil. Generally, mineral lubricating oils having an SUS viscosity at 100° F. between 50 and 1000 may be used in the formulation of the improved lubricants of this invention although the viscosity range will usually fall between 70 and 300 SUS at 100° F. A blend of base oils can be employed to provide a suitable base oil for either a single or multigrade motor oil; for example, a naphthenic oil of an SUS viscosity of about 145 at 100° F. and naphthenic lubricating oil of an SUS viscosity of about 100 at 100° F. A desirable base oil blend may be formulated, in addition, from a 65 percent of a furfural-refined, acid-treated clay-contacted, solvent-dewaxed, paraffin base distillate having an SUS at 100° F. of 100; a viscosity index of about 100, a flash point (Cleveland Open Cup Method) of about 385° F. and a pour point below 0° F. or +10° F.; 22 percent of an acid-treated naphthenic base having an SUS at 100° F. of 60, a flash above 300° F. and a pour below −40° F. and 13 percent of a paraffin base residuum which has been propane-deasphalted, solvent-dewaxed and clay-contacted and which has an SUS viscosity at 210° F. of 160, a flash of about 540° F. and a pour below 50° F. This base oil mixture has a flash above 375° F., a pour below 0° F. and a viscosity index of about 93. Viscosity index is measured according to ASTM D 2270; viscosity at 100° F. and 210° F. is determined using ASTM D 445; and pour point data is arrived at utilizing ASTM D 97.

A fully formulated crankcase or automatic transmission lubricant composition for use herein will comprise a base oil blend such as the foregoing in an amount of at least 77 weight percent to about 99 weight percent (e.g. 99.05 weight percent) and preferably about 99 percent (e.g. 89.46 weight percent) and will contain from about 0.5 to 8 weight percent (e.g. 5 weight percent) of an oil concentrate containing about 35 percent by weight of a bsic amino nitrogen-containing addition type of alkyl ester of methacrylic acid, that is, butyl, lauryl, stearyl and dimethyl amino-ethyl methacrylates in approximately 21:53:22:4 weight ratios (as described in U.S. Pat. No. 2,737,496); from about 0.005 to 0.25 percent by weight of a dimethyl silicone anti-foaming agent; from 0.1 to 3.0 percent of a zinc dialkyl dithiophosphate such as described hereinabove; an overbased calcium sulfonate in an amount by weight based on (calcium content) of 0.2 to 2 wt. percent; an ethylene-propylene copolymer as a viscosity index improver in an amount by weight of 5 percent to 15 percent; a conventional naphthyl amine antioxidant in a concentration of 0.1 to 10 percent; and about 0.1 to 5, and desirably about 2.5, weight percent of an oil concentrate (containing about 44 percent by weight of a naphthenic lubricating oil of an SUS viscosity of about 100 at 100° F.) of mono (beta-hydroxyethyl) alkene thiophosphonate; and 0.1 to 10, and preferably 0.1 to 6, weight percent, illustratively 0.54 weight percent, as indicated above, of the lactam of the invention.

The formulations so derived are supplied by standard procedures to the crankcase of the engine. In accordance with the invention, the corrosion inhibition which would occur in the absence of the lactam acids of the invention will be found to be significantly alleviated by their presence.

The present invention is further illustrated by the following examples:

EXAMPLE I

This example illustrates the preparation of the gamma-lactam acid, 2(3)-tetrapropenyl-3-carboxy-4-phenyl-5-methyl butyrolactam.

Equimolar proportions of the imino-containing compound, N-methylbenzylidenimine (benzylidene-methylamine) and dodecenyl succinic anhydride were admixed at room temperature and heated to 120° C. under a $N_2$-atmosphere and these reaction conditions sustained for a period of 5 hours until the imine reactant was consumed as determined by $HClO_4$ titration. The products were vacuum stripped at 120° C., initially to 15 millimeters of mercury (mm Hg) and sequentially at 0.5 to 1.5 mm. The product, an isomeric mixture, gave the following analysis:

| Analysis | Found | Calculated |
|---|---|---|
| Percentage (% N) | 3.61 | 3.64 |
| Total Acid Number (TAN) | 116 | 146 |
| Saponification Number (SAP No.) | 163.4 | 146 |
| Percentage of basis N as determined by $HClO_4$ titration (% basic N) | 0.07 | 0 |

The foregoing TAN value indicated that 80 mol weight percent of the product lactam acid, 2(3)-tetrapropenyl or dodecenyl 3-carboxy-4-phenyl-5-methyl butryolactam was produced.

EXAMPLE II

This example illustrates the preparation of the gamma-lactam acid, 2(3)-polybutenyl-3-carboxy-4-phenyl-5-methyl butyrolactam.

Equimolar proportions of polybutenyl succinic anhydride (wherein the polybutenyl substituent has a molecular weight of about 1290) and N-methyl benzylidenimine were admixed at a temperature of 80° C. because of the anhydride's relatively high viscosity and heated to 120° C. for 5 hours until the imine was consumed as determined by $HClO_4$ titration. The products were vacuum stripped at 120° C., first to about 15 mm. and thereafter to 0.5 to 1.5 mm. The product evidenced the following properties upon analysis:

| Analysis | Found | Calculated |
|---|---|---|
| % N | 0.63 | 0.67 |
| TAN | 17.3 | 27 |
| SAP. No. | 32.8 | 27 |
| % Basic N | | |

| Analysis | Found | Calculated |
|---|---|---|
| ($HClO_4$ titration) | 0.014 | 0 |

The TAN value reflected a conversion to the desired lactam acid, 2(3)-polybutenyl-3-carboxy-4-phenyl-5-methyl butyrolactam.

EXAMPLE III

This example illustrates the production of the gamma-lactam acid, 1',2'-ethylene-bis-[2(3)-polybutenyl-3-carboxy-4-phenyl-butyrolactam-5].

The Schiff's base, ethylene bis-benzylidenimine, prepared by reaction of benzaldehyde and ethylenediamine, in standard manner, was reacted with the polybutenyl succinic acid anhydride of Example II in the manner described in that Example in a mole ratio of imine to anhydride of 1:2, respectively, to form the N,N'-alkylene-bis-acid, 1',2'-ethylene-bis-[2(3)-polybutenyl-3-carboxy-4-phenyl butyrolactam-5]. This desired product was recovered by vacuum stripping in the manner recited in Example II. Its analysis was as follows:

| Analysis | Found | Calculated |
|---|---|---|
| % N | 0.34 | 0.38 |
| Total Base Number (TBN) | 2.9 | 0 |
| TAN | 8.0 | 15.0 |
| SAP. No. | 22.4 | 15.0 |

The percentage conversion to lactam acid was indicated to be 70 mol weight percent based on the amount of benzaldehyde recovered in a side reaction.

EXAMPLE IV

This example illustrates the preparation of the bis-lactam-bis-acid, 1',6'-hexylene-bis-[2(3)-polybutenyl-3-carboxy-4-phenyl butyrolactam-5].

The Schiff's base, hexylene-bis-benzylidenimine, prepared by reaction of benzaldehyde and hexamethylenediamine using known procedures, was reacted with polybutenyl succinic anhydride having a molecular weight of about 1300 in a mol ratio of imine to anhydride of 1:2 respectively according to the procedure of Example II to yield the gamma-lactam acid, 1',6'-hexylene-bis-[2(3)-polybutenyl-3-carboxy-4-phenyl-butyrolactam-5]. The analysis was as follows:

| Analysis | Found | Calculated |
|---|---|---|
| % N | 0.31 | 0.37 |
| TBN | 2.1 | 0 |
| TAN | 10.0 | 15.0 |
| SAP. No. | 14.8 | 15.0 |

The conversion to lactam acid was determined to be 86 mol weight percent on the basis of the amount of benzaldehyde recovered.

EXAMPLE V

This example demonstrates the preparation of 2(3)-polybutenyl-3-carboxy-4-phenyl-5-(N,N-dimethylaminoethyl) butyrolactam according to the invention.

3-(N',N'-dimethylamino) propyl N-benzylidenimine, prepared by the reaction of substantially equimolar proportions of benzaldehyde and N,N-dimethylaminopropylamine by known procedures, was reacted in turn in equimolar proportions with the polybutenyl succinic anhydride of Example IV and the reaction carried forward by the method of Example II to form a reaction product which was vacuum-stripped from the reaction product mixture also in the manner of Example II. The product was determined by analysis to be 2(3)-polybutenyl-3-carboxy-4-phenyl-4-(N,N-dimethylaminoethyl) butyrolactam. The analysis was as follows:

| Analysis | Found | Calculated |
|---|---|---|
| % N | 0.67 | 0.73 |
| TBN | 15.7 | 14.7 |
| TAN | 7.2 | 14.7 |
| SAP. No. | 19.2 | 14.7 |

The conversion to the lactam acid product was found to be about 65 mol weight percent as determined on the basis of the amount of benzaldehyde recovered.

The analyses of Examples III, IV, and V, with infrared confirmation of the lactam carbonyl group present, show that the major portion of the benzylidene amine moieties were converted to lactam acid in each instance.

EXAMPLE VI

This example evidences the effectiveness of the lactam additives of the invention, 2(3)-tetrapropenyl-3-carboxy-4-phenyl-4-methyl butyrolactam of Example I ("dodecenyl lactam acid") and 2(3)-polybutenyl-3-carboxy-4-phenyl-5-methyl butyrolactam of Example II ("polybutenyl lactam acid") as corrosion inhibitors and dispersants.

The additives of the invention, dodecenyl lactam acid and polybutenyl lactam acid, were incorporated in the amounts indicated in Table I appearing hereinafter in conventional crankcase lubricating oil compositions also characterized in Table I and subjected to a standard "Bench Rust Test" procedure wherein a section of a push rod and a sample of the test oil, e.g., the base blend and additive of the invention in the concentrations indicated, is put in a vessel which is, in turn, placed in a heated bath to maintain the temperature of the test oil at a moderately elevated temperature. A nitrogen dioxide-air stream and an air stream saturated with water vapor are passed through the test oil for a fixed period of time. After the first hour of the test, small amounts of high-lead, high-sulfur fuel are also added to the test oil at regular intervals. On completion of the test, the push rod is removed from the test oil, washed with solvent to remove oil and varnish, and then visually rated for rust using the CRF rust rating scale (a scale from 10 to 1, with 10 being clean); a value of about 8 to 10 representing a clearly acceptable corrosion inhibition. The results of a control run of the base blend alone tested in like manner with the base blend formulations including the lactam acids of the invention are shown in Table I. Percentages are by weight of the indicated component present in the following Table:

Table I

| | Run | | |
|---|---|---|---|
| | 1 | 2 | 3 |
| Composition (in SNO-7) | | | |
| CO₂ neutralized overbased Ca sulfonate - % Ca | 0.23 | 0.23 | 0.23 |
| Zinc alkyldithiophosphate prepared mixed isopropanol and P₂S₅ - % Zn | 0.15 | 0.15 | 0.15 |
| Mixed alkylated tri-substituted diphenyl amine (VANLUBE Na) | 0.25 | 0.25 | 0.25 |
| Ethylene-propylene copolymer of 20,000–50,000 molecular weight containing 30 to 50 mol % propylene in a mineral oil pale stock and prepared (according to U.S. Pat. No. 3,522,180) | 10.0 | 10.0 | 10.0 |
| Copolymer of synthetic lauryl methacrylate stearyl methacrylate in a weight ratio of 75:25 respectively on the basis of monomer charged and incorporated in a mineral pale stock | 0.5 | 0.5 | 0.5 |
| Dodecenyl lactam acid | 0 | 1.0 | 0 |
| Polybutenyl lactam acid | 0 | 0 | 5.0 |
| Test Procedure | | | |
| Corrosion Inhibition | 6.5 | 8.3 | 7.6 |

The foregoing results demonstrate clearly that the lactam acids impart a significantly superior corrosion inhibition to crankcase lubricant compositions; and that, in addition, the dodecenyl lactam acid is materially superior to the polybutenyl lactam acid in this regard.

It will be evident that the terms and expressions which have been employed are used as terms of description and not of limitation. There is no intention in the use of such terms and expressions of excluding equivalents of the features shown and described or portions thereof and it is recognized that various modifications are possible within the scope of the invention claimed.

What is claimed is:

1. A lubricant oil composition comprising an oil of lubricating viscosity, and an effective dispersant and rust inhibiting amount of an isomeric mixture of a lactam acid, said lactam acid being selected from the group consisting of:
    1. 2(3) polybutenyl-3-carboxy-4-phenyl-5(N,N-dimethylaminopropyl) butyrolactam, in which said polybutenyl radical has from 10 to 300 carbon atoms,
    2. 1,2-ethylene bis[2(3) polybutenyl-3-carboxy-4-phenyl-butyrolactam-5] in which said polybutenyl radical has from 10 to 300 carbon atoms, and
    3. 1,6-hexylene bis[2(3) polybutenyl-3-carboxy-4-phenyl-butyrolactam-5] in which said polybutenyl radical has from 10 to 300 carbon atoms.

2. A lubricant oil composition as claimed in claim 1 wherein said lactam acid is 1,2-ethylene bis-[2(3)-polybutenyl-3-carboxy-4-phenyl butyrolactam-5].

3. A lubricant oil composition as claimed in claim 1 wherein said lactam acid is 1,6-hexylene-bis-[2,(3)-polybutenyl-3-carboxy-4-phenyl butyrolactam-5].

4. A lubricant oil composition as claimed in claim 1 wherein said lactam acid is 2(3)-polybutenyl-3-carboxy-4-phenyl-5(N,N-dimethylaminopropyl) butyrolactam.

5. A lactam acid selected from the group consisting of:
1. 2(3) polybutenyl-3-carboxy-4-phenyl-5(N,N-dimethylaminopropyl) butyrolactam, in which said polybutenyl radical has from 10 to 300 carbon atoms,
2. 1,2-ethylene bis[2(3) polybutenyl-3-carboxy-4-phenyl-butyrolactam-5] in which said polybutenyl radical has from 10 to 300 carbon atoms, and
3. 1,6-hexylene bis[2(3) polybutenyl-3-carboxy-4-phenyl-butyrolactam-5] in which said polybutenyl radical has from 10 to 300 carbon atoms.

6. A lactam acid as claimed in claim 5 wherein said acid is 1,2-ethylene-bis-[2 or 3-alkenyl-3-carboxy-4-phenyl butyrolactam-5].

7. A lactam acid as claimed in claim 5 wherein said acid is 1,6-hexylene-bis-[2 or 3-alkenyl-3-carboxy-4-phenyl butyrolactam-5].

8. A lactam acid as claimed in claim 5 wherein said acid is 2 or 3-alkenyl-3-carboxy-4-phenyl-5(N,N-dimethylaminopropyl) butyrolactam.

9. A lactam acid as claimed in claim 5 wherein said acid is 1',2'-ethylene bis[2-polybutenyl-3-carboxy-4-phenyl butyrolactam-5].

10. A lactam acid as claimed in claim 5 wherein said acid is 1',6'-hexylene-bis-[2-polybutenyl-3-carboxy-4-phenyl butyrolactam-5].

11. A lactam acid as claimed in claim 5 wherein said acid is 2-polybutenyl-3-carboxy-4-phenyl-5-(N,N-dimethylaminopropyl) butyrolactam.

* * * * *